US011377670B2

(12) United States Patent
Xing et al.

(10) Patent No.: US 11,377,670 B2
(45) Date of Patent: Jul. 5, 2022

(54) METHOD FOR PREPARING VANILLIN BY FERMENTATION WITH EUGENOL AS SUBSTRATE

(71) Applicant: Xiamen Oamic Biotechnology Co., Ltd., Fujian (CN)

(72) Inventors: Chenguang Xing, Fujian (CN); Xijing Zhao, Fujian (CN); Yarou Zeng, Fujian (CN); Huanyan Lan, Fujian (CN); Wei Liu, Fujian (CN); Gang Liu, Fujian (CN); Zhimin Deng, Fujian (CN)

(73) Assignee: Xiamen Oamic Biotechnology Co., Ltd., Xiamen (CN)

( * ) Notice: Subject to any disclaimer, the term of this patent is extended or adjusted under 35 U.S.C. 154(b) by 0 days.

(21) Appl. No.: 17/137,464

(22) Filed: Dec. 30, 2020

(65) Prior Publication Data

US 2021/0198703 A1 Jul. 1, 2021

(30) Foreign Application Priority Data

Dec. 31, 2019 (CN) ......................... 201911424942.1

(51) Int. Cl.

| | |
|---|---|
| ***C12P 7/24*** | (2006.01) |
| ***C12N 1/20*** | (2006.01) |
| ***C12N 1/14*** | (2006.01) |
| *C12R 1/125* | (2006.01) |
| *C12R 1/80* | (2006.01) |

(52) U.S. Cl.

CPC ................ *C12P 7/24* (2013.01); *C12N 1/145* (2021.05); *C12N 1/205* (2021.05); *C12R 2001/125* (2021.05); *C12R 2001/80* (2021.05)

(58) Field of Classification Search

CPC .......... C12R 2001/80; C12R 2001/125; C12N 1/145; C12N 1/205; C12P 7/24

See application file for complete search history.

(56) References Cited

U.S. PATENT DOCUMENTS

2002/0182697 A1 12/2002 Steinbuchel et al.

FOREIGN PATENT DOCUMENTS

| | | | |
|---|---|---|---|
| CN | 104769121 | A | 7/2015 |
| CN | 105838626 | A | 8/2016 |
| CN | 106591390 | A | 4/2017 |
| CN | 110257312 | A | 9/2019 |
| WO | 9502062 | A1 | 1/1995 |
| WO | 2000026355 | A2 | 5/2000 |
| WO | 2012172108 | A1 | 12/2012 |
| WO | 2015066722 | A1 | 5/2015 |

OTHER PUBLICATIONS

Kaur, B., & Chakraborty, D. (2013). Biotechnological and molecular approaches for vanillin production: a review. Applied Biochemistry and Biotechnology, 169(4), 1353-1372 (Year: 2013).*

Zhao, et al, "Biotransformation of isoeugenol to vanillin by a novel strain of Bacillus fusiformis", Biotechnology Letters (2005) 27: 1505-1509.

Achterholt, et al., "Identification of *Amycolatopsis* sp. strain HR167 genes, involved in the bioconversion of ferulic acid to vanillin", Accepted: May 19, 2000, Appl Microbiol Biotechnol (2000) 54: 799-807.

"Highly Efficient Biotransformation of Eugenol to Ferulic Acid and Further Conversion to Vanillin in Recombinant Strains of *Escherichia coli*", Nov. 2003, Jorg Overhage, Alexander Steinbuchel and Horst Priefert, Applied and Environmental Microbiology, vol. 69, No. 11, pp. 6569-6576.

"A Rapid Colorimetric Screening Method for Vanillic Acid and Vanillin-producing Bacterial Strains", 2013, N.A. Zamzuri, S. Abd-Aziz, R.A. Rahim, L.Y. Phang, N.B. Alitheen and T. Maeda, Journal of Applied Microbiology, vol. 116, pp. 903-910.

"Vanillin-Bioconversion and Bioengineering of the Most Popular Plant Flavor and its De Novo Biosynthesis in the Vanilla Orchid", Jan. 2015, Nethaji J. Gallage and Birger Lindberg Moller, Molecular Plant Review Article, vol. 8, Issue 1, 35 pgs.

* cited by examiner

*Primary Examiner* — Louise W Humphrey
*Assistant Examiner* — Trevor L Kane
(74) *Attorney, Agent, or Firm* — Cooper Legal Group, LLC

(57) ABSTRACT

The present disclosure discloses a method for preparing vanillin by fermentation with eugenol as a substrate, preparing vanillin by a mixed fermentation of *Penicillium simplicissimum* OMK-68 and *Bacillus* sp. OMK-69, its potency reached 35 g/L, the mass conversion rate of eugenol reaches 83.3%. *Penicillium simplicissimum* OMK-68 in the present disclosure can use eugenol as a substrate for fermentation to prepare coniferyl alcohol, and its fermentation effect and substrate utilization rate are far better than wild-type *Penicillium simplicissimum.* The *Bacillus* sp. OMK-69 in the present disclosure can use coniferyl alcohol as a substrate for fermentation to prepare vanillin, and its fermentation effect and substrate utilization rate are far better than wild-type *Bacillus* sp.

11 Claims, 3 Drawing Sheets

METHOD FOR PREPARING VANILLIN BY FERMENTATION WITH EUGENOL AS SUBSTRATE

RELATED APPLICATIONS

This application claims priority to Chinese patent application number 201911424942.1, filed on Dec. 31, 2019. Chinese patent application number 201911424942.1 is incorporated herein by reference.

FIELD OF THE DISCLOSURE

The present disclosure relates to vanillin preparation, and in particular, relates to a method for preparing vanillin by fermentation with eugenol as a substrate.

BACKGROUND OF THE DISCLOSURE

Vanillin is currently one of the most used food flavoring agents in the world. It is known as the "king of food flavors" and is one of the world's most popular flavors until 2019.

Vanillin naturally exists in plants, such as vanilla beans. Vanillin can be extracted from the pods of tropical vanilla orchids. As vanilla orchid pod plants have very specific requirements for soil and climatic conditions and the natural processing technology is complex, the natural source of vanillin is very limited. Vanillin products extracted from natural plants account for less than 1% of global production.

In order to meet the needs of the market, people began to develop research on the biosynthesis of vanilla. Early on, Achterholt et al. developed a process for the biosynthesis of vanillin with ferulic acid as a substrate. Biological conversion of ferulic acid to synthesize vanillin is the most mature process for biosynthesis of vanillin. Later, people also studied the accumulation of vanillin through microbial metabolism with eugenol as a substrate. WO/2000/026355 discloses that using *Pseudomonas* sp. HR199 is used to biotransform eugenol to prepare 2.6 g/L vanillin. Zhao, L. Q. and others studied the use of *Bacillus fusiformis* SW-B9 to metabolize isoeugenol to prepare 32.5 g/L vanillin and so on.

BRIEF SUMMARY OF THE DISCLOSURE

The present disclosure provides a method for preparing vanillin by fermentation using eugenol as a substrate.

The present disclosure provides the following specific technical solution:

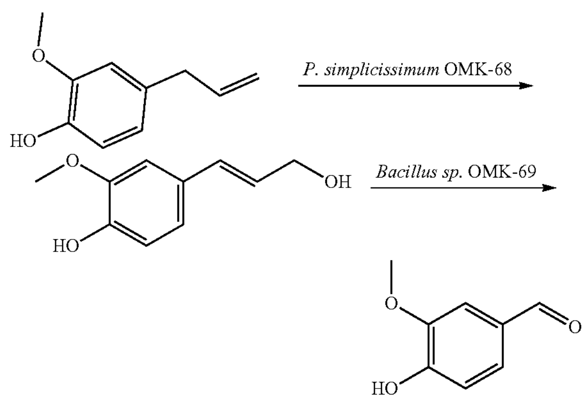

A first technical solution of the present disclosure is as follows:

A method for preparing vanillin by fermentation with eugenol as a substrate, preparing vanillin by a mixed fermentation of *Penicillium simplicissimum* OMK-68 and *Bacillus* sp. OMK-69;

The *Penicillium simplicissimum* OMK-68 was deposited at the China Center for Type Culture Collection, located at Wuhan University, Wuhan, China, on Oct. 16, 2019, with the deposit number is CCTCC NO: M 2019827. The *Bacillus* sp. OMK-69 was deposited at the China Type Culture Collection, located at Wuhan University, Wuhan, China, on Oct. 16, 2019, with the deposit number is CCTCC NO: M 2019826.

In a preferred embodiment, the method comprises the following steps:

(1) culturing the *Penicillium simplicissimum* OMK-68 and the *Bacillus* sp. OMK-69 on sterile yeast extract peptone dextrose (YPD) plates, and then activating by a first seed culture medium and a second seed culture medium respectively to obtain the *Penicillium simplicissimum* OMK-68 seed liquid and the *Bacillus* sp. OMK-69 seed liquid;

(2) inoculating the *Penicillium simplicissimum* OMK-68 seed liquid into a sterile fermentation culture medium, and fermenting in a fermenter for 10-13 hours;

(3) inoculating the *Bacillus* sp. OMK-69 seed liquid into the material obtained in step (2), and continually fermenting in the fermenter for 9-11 hours;

(4) adding eugenol, functioning as a substrate, into the material obtained in step (3), then adding the same amount of eugenol as the first addition every 3-5 hours for 5-7 times in total, and a cumulative amount of eugenol is 39-45 g/L; and (5) purifying the material obtained in step (4) to obtain the vanillin.

In a preferred embodiment, a composition of the first seed culture medium comprises 28-32 g/L malt extract, 13-16 g/L yeast powder, 8-12 g/L peptone, 1.1-1.3 g/L potassium dihydrogen phosphate, 0.7-0.9 g/L sodium chloride, a solvent is water, and pH is natural pH.

In a preferred embodiment, a composition of the second seed culture medium comprises 18-22 g/L glucose, 9-11 g/L yeast powder, 8-12 g/L peptone, 0.7-0.9 g/L dipotassium hydrogen phosphate, 0.7-0.9 g/L sodium chloride, a solvent is water, and pH is natural pH.

In a preferred embodiment, a composition of the sterile fermentation culture medium comprises 28-32 g/L glucose, 18-21 g/L yeast powder, 14-16 g/L peptone, 0.25-0.32 g/L magnesium sulfate, 0.9-1.1 g/L potassium dihydrogen phosphate, 0.7-0.9 g/L sodium chloride, 0.9-1.1 g/L ammonium sulfate, a solvent is water, and pH is natural pH.

A second technical solution of the present disclosure is as follows:

*Penicillium simplicissimum* OMK-68 deposited at the China Center for Type Culture Collection, located at Wuhan University, Wuhan, China, on Oct. 16, 2019, with the deposit number of CCTCC NO: M 2019827.

A use of the *Penicillium simplicissimum* OMK-68 in a preparation of coniferyl alcohol using eugenol as a substrate.

A third technical solution of the present disclosure is as follows:

*Bacillus* sp. OMK-69 deposited at the China Center for Type Culture Collection, located at Wuhan University, Wuhan, China, on Oct. 16, 2019, with the deposit number of CCTCC NO: M 2019826.

A use of the *Bacillus* sp. OMK-69 in a preparation of vanillin using coniferyl alcohol as a substrate.

Compared with the existing techniques, the technical solution has the following advantages.

1. The method of the present disclosure obtains vanillin through mixed fermentation of *Penicillium simplicissimum* OMK-68 and *Bacillus* sp. OMK-69, and the mass conversion rate of eugenol reaches 83.3%.

2. *Penicillium simplicissimum* OMK-68 in the present disclosure can use eugenol as a substrate for fermentation to prepare coniferyl alcohol, and its fermentation effect and substrate utilization rate are far better than wild-type *Penicillium simplicissimum.*

3. The *Bacillus* sp. OMK-69 in the present disclosure can use coniferyl alcohol as a substrate for fermentation to prepare vanillin, and its fermentation effect and substrate utilization rate are far better than wild-type *Bacillus* sp.

DETAILED DESCRIPTION OF THE EMBODIMENTS

The present disclosure will be further described below in combination with the accompanying drawings and embodiments.

Embodiment 1

Figure 1:
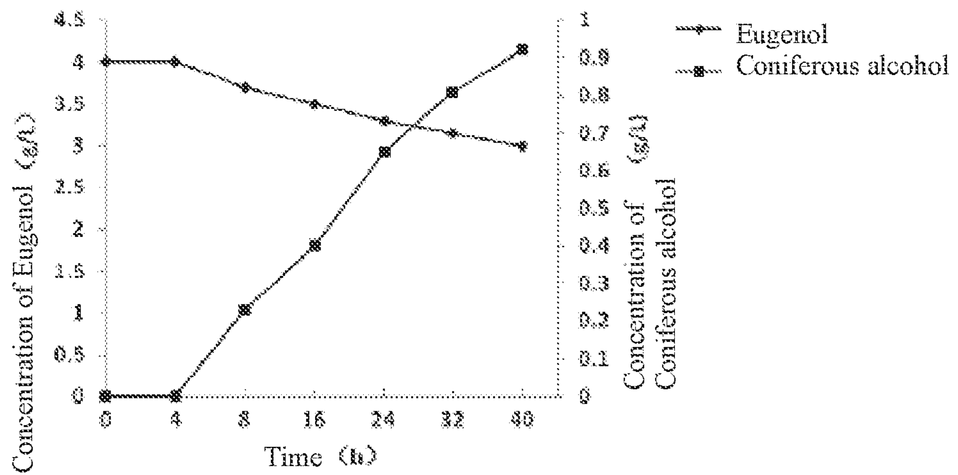
FIG. 1 illustrates a fermentation result graph of the wild-type strain *Penicillium simplicissimum* in the present disclosure.
Figure 2:
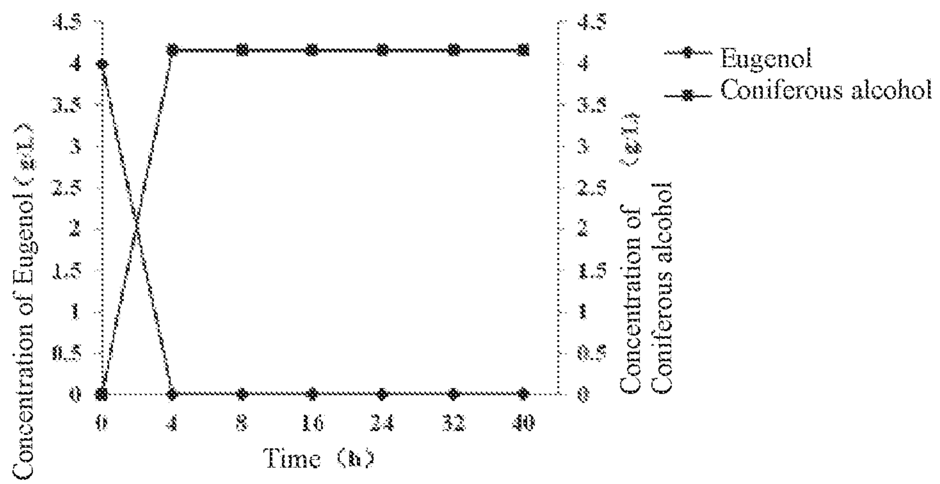
FIG. 2 illustrates a fermentation result graph of *Penicillium simplicissimum* OMK-68 in Embodiment 1 of the present disclosure.

In the present disclosure, a strain *Penicillium simplicissimum* (i.e., a wild-type strain *Penicillium simplicissimum*) that prepares coniferous alcohol by metabolizing eugenol is one of strains *Penicillium simplicissimum* that prepare coniferous alcohol by metabolizing eugenol and were selected from numerous microorganisms in a marine mud bed. In this embodiment, a single chemical mutagenesis reagent or mixed chemical mutagenesis reagents were used on the strain *Penicillium simplicissimum* to perform multiple rounds of chemical mutagenesis. At the same time, a reasonable strain screening method was used to finally screen out a mutant strain *Penicillium simplicissimum* OMK-68 that efficiently prepares coniferyl alcohol by metabolizing eugenol. The wild-type strain *Penicillium simplicissimum* and the mutant strain *Penicillium simplicissimum* OMK-68 were fermented by the same fermentation process, and the results are respectively shown in FIGS. 1 and 2.

A strain *Bacillus* sp. (i.e., a wild-type strain *Bacillus* sp.) that prepares vanillin by metabolizing coniferous alcohol is one of strains *Bacillus* sp. that prepare vanillin by metabolizing coniferous alcohol and were selected from numerous microorganisms in the marine mud bed. A specific screening method is as follows:

100 mg/L of coniferyl alcohol was added into a broth agar medium and was sterilized at 121° C. for 20 minutes, after a temperature of the broth agar medium was cooled to about 60° C., a preset amount of 2,4-dinitrophenylhydrazine was added and mixed evenly, a plate was configured, then microorganisms in the marine mud bed were spread on the plate, and pink colonies were finally selected.

Figure 3:
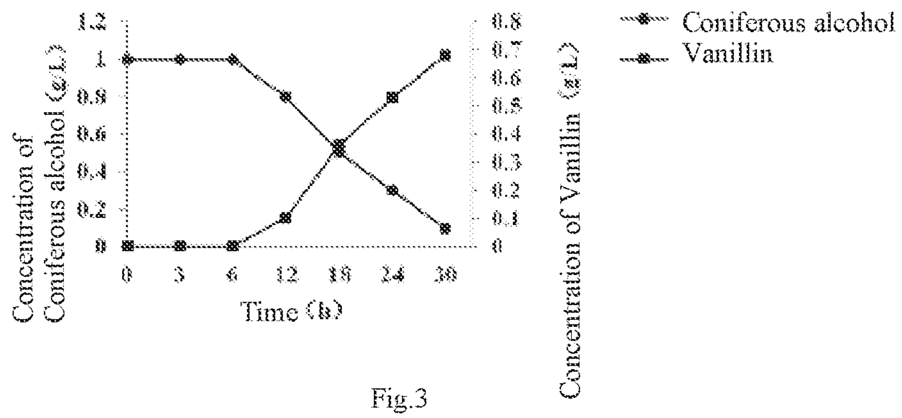
FIG. 3 illustrates a fermentation result graph of the wild-type strain *Bacillus* sp. in the present disclosure.
Figure 4:
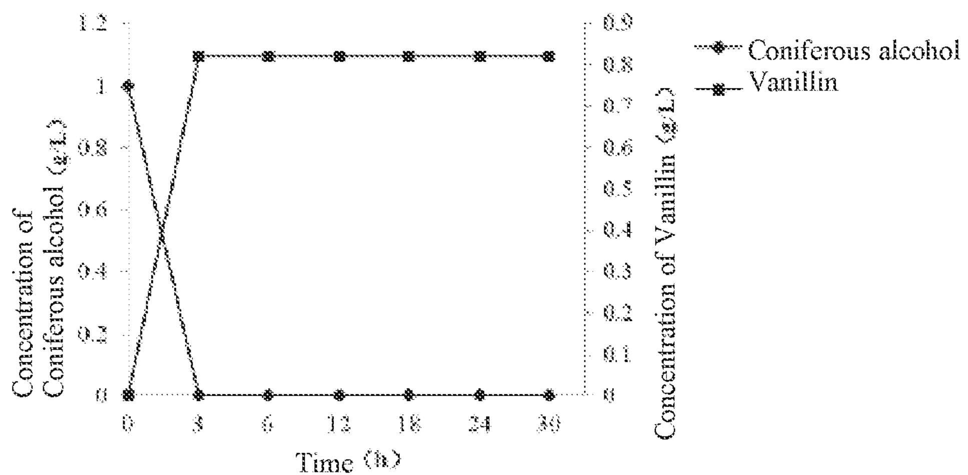
FIG. 4 illustrates a fermentation result graph of *Bacillus* sp. OMK-69 in Embodiment 1 of the present disclosure.

Like *Penicillium simplicissimum* OMK-68, a single chemical mutagenesis reagent or mixed chemical mutagenesis reagents were used on the strain *Bacillus* sp. (i.e., the wild-type strain *Bacillus* sp.) to perform multiple rounds of chemical mutagenesis. At the same time, a reasonable strain screening method was used to finally screen out a mutant strain *Bacillus* sp. OMK-69 that efficiently prepares vanillin by metabolizing coniferyl alcohol. The wild-type strain *Bacillus* sp. and the mutant strain *Bacillus* sp. OMK-69 were fermented by the same fermentation process, and the results are respectively shown in FIGS. 3 and 4.

The *Penicillium simplicissimum* OMK-68 was deposited in China Center for Type Culture Collection (CCTCC), located at Wuhan University, Wuhan, China under the Budapest Treaty and made available to the public on Oct. 16, 2019 with deposit number CCTCC NO: M 2019827.

The *Bacillus* sp. OMK-69 was deposited in China Center for Type Culture Collection (CCTCC), located at Wuhan University, Wuhan, China under the Budapest Treaty and made available to the public on Oct. 16, 2019 with deposit number CCTCC NO: M 2019826.

Embodiment 2

(1) Activation on a plate: a tube of glycerin and the strain *Penicillium simplicissimum* OMK-68 refrigerated in a refrigerator at −80° C. was taken, the strain *Penicillium simplicissimum* OMK-68 was streaked on a YPD plate, and the YPD plate was placed in an incubator at 30° C. for 72 hours until colonies are full.

(2) Seed culture: a single colony from the plate for activation was inoculated into a 3 L bioreactor containing 1.8 L first seed culture medium and was cultured in a shaker at 30° C. and 300 rpm for 24 hours during ventilation status. After no other bacteria is observed by microscope, seed liquid was obtained and was ready to be inoculated in a fermenter. Compositions of the first seed culture medium are shown in Table 1:

TABLE 1

| Name | Concentration (g/L) |
|---|---|
| malt extract powder | 30 |
| yeast powder | 15 |
| peptone | 10 |
| potassium dihydrogen phosphate | 1.2 |
| sodium chloride | 0.8 |
| pH | Nature (i.e., no pH adjustment) |

Figure 5:
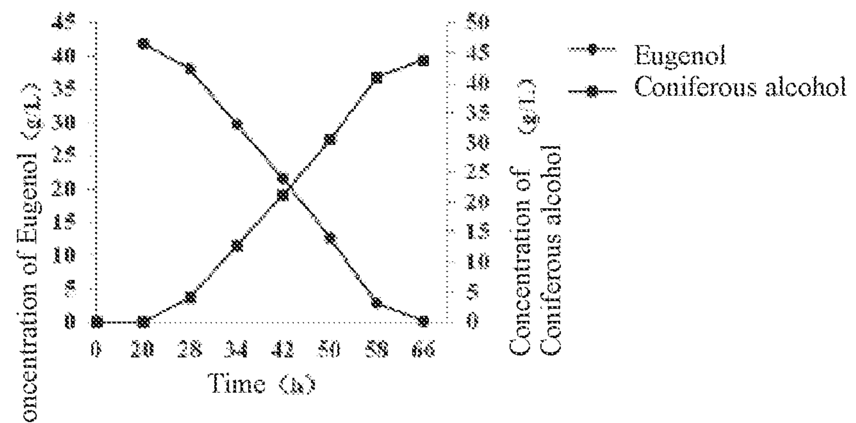
FIG. 5 illustrates a fermentation result graph of *Penicillium simplicissimum* OMK-68 in Embodiment 2 of the present disclosure.

(3) 1.8 L of the seed liquid obtained in step (2) was inoculated into 10.2 L first fermentation culture medium (i.e., a first sterile fermentation medium, sterilized at 121° C. for 30 min) in a 20 L fermenter and was fermented at 30° C. A stirring rotation speed was 400 rpm, and a ventilation ratio was 1:0.2 during the fermentation. After 20 hours of fermentation, 42 g/L of a eugenol (504 g in total) substrate was added and was continually fermented for 48 hours. After the fermentation is completed, a fermentation solution was obtained, a concentration of coniferyl alcohol in the fermentation solution detected by high-performance liquid chromatography (HPLC) was 43.7 g/L. The result is shown in FIG. 5. Compositions of the first fermentation culture medium are shown in Table 2:

TABLE 2

| Name | Concentration (g/L) |
|---|---|
| yeast powder | 10 |
| peptone | 5 |
| magnesium sulfate | 0.2 |
| potassium dihydrogen phosphate | 1.0 |
| sodium chloride | 0.8 |
| ammonium sulfate | 0.5 |
| pH | Nature |

Embodiment 3

(1) Activation on a plate: a tube of glycerin and the strain *Bacillus* sp. OMK-69 refrigerated in a refrigerator at −80° C. was taken, the strain *Bacillus* sp. OMK-69 was streaked on a YPD plate, and the YPD plate was placed in an incubator at 30° C. for 24 hours until colonies are full;

(2) Seed culture: a single colony from the plate for activation was inoculated into a 3 L bioreactor containing 1.8 L second seed culture medium, and was cultured in a shaker at 30° C. and 400 rpm for 24 hours during ventilation status; after no other bacteria is observed by microscope, seed liquid was obtained and was ready to be inoculated in a fermenter. Compositions of the second seed culture medium are shown in Table 3:

TABLE 3

| Name | Concentration (g/L) |
|---|---|
| glucose | 20 |
| yeast powder | 10 |
| peptone | 10 |
| dipotassium hydrogen phosphate | 0.8 |
| sodium chloride | 0.8 |
| pH | nature |

Figure 6:
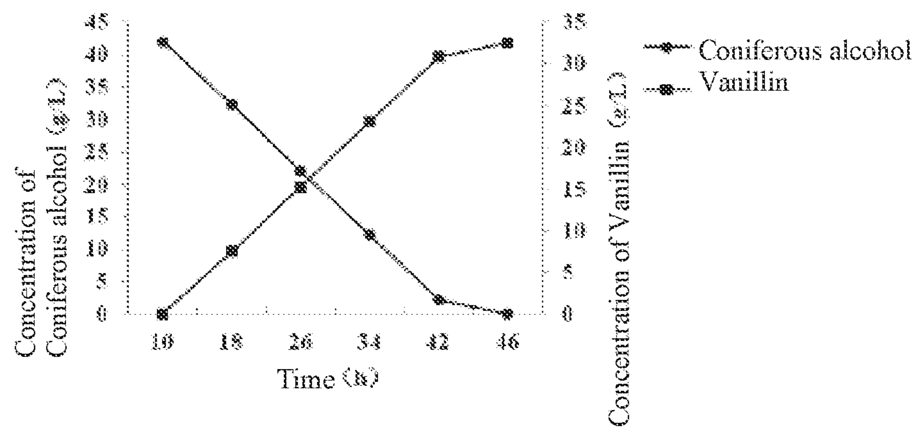
FIG. 6 illustrates a fermentation result graph of *Bacillus* sp. OMK-69 in Embodiment 3 of the present disclosure.

(3) 1.8 L of the seed liquid obtained in step (2) was inoculated into 10.2 L second fermentation culture medium (i.e., a second sterile fermentation medium, sterilized at 121° C. for 30 min) in a 20 L fermenter and was fermented at 30° C. A stirring rotation speed was 500 rpm, and a ventilation ratio was 1:0.3 during the fermentation. After 10 hours of fermentation, 42 g/L of a coniferyl alcohol (504 g in total) substrate was added and was continually fermented for 36 hours. After the fermentation is completed, a fermentation solution was obtained, a concentration of vanillin in the fermentation solution detected by HPLC was 32.5 g/L. The result is shown in FIG. 6. Compositions of the second fermentation culture medium are shown in Table 4:

TABLE 4

| Name | Concentration (g/L) |
|---|---|
| glucose | 30 |
| yeast powder | 8.0 |
| peptone | 2.0 |
| magnesium sulfate | 0.2 |
| potassium dihydrogen phosphate | 1.0 |
| sodium chloride | 0.8 |
| ammonium sulfate | 0.5 |
| pH | nature |

Embodiment 4

(1) Activation on a plate: a tube of glycerin and the strain *Penicillium simplicissimum* OMK-68 refrigerated in a refrigerator at −80° C. was taken, the strain *Penicillium simplicissimum* OMK-68 was streaked on a YPD plate, and the YPD plate was placed in an incubator at 30° C. for 72 hours until colonies are full; a tube of glycerin and the strain *Bacillus* sp. OMK-69 refrigerated in a refrigerator at −80° C. was taken, the strain *Bacillus* sp. OMK-69 was steaked on a YPD plate, and the YPD plate was placed in an incubator at 30° C. for 24 hours until colonies are full;

(2) Seed culture: seed culture of the *Penicillium simplicissimum* OMK-68 is the same as in step (2) of Embodiment 2, and seed culture of the *Bacillus* sp. OMK-69 is the same as in step (2) of Embodiment 3.

Figure 7:
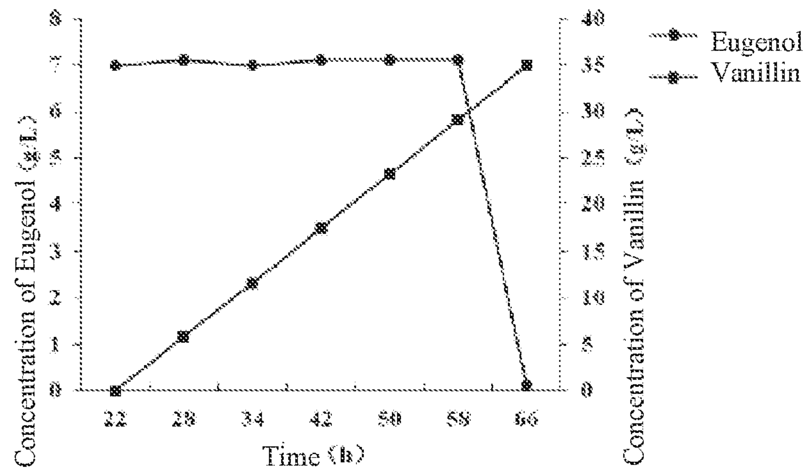
FIG. 7 illustrates a fermentation result graph of a mixture of *Penicillium simplicissimum* OMK-68 and *Bacillus* sp. OMK-69 in Embodiment 4 of the present disclosure.

(3) 1.8 L of the seed liquid of *Penicillium simplicissimum* OMK-68 obtained in step (2) was inoculated into 8.4 L fermentation culture medium (sterilized at 121° C. for 30 min) in a 20 L fermenter and was fermented at 30° C., the fermentation conditions were that a stirring rotation speed of 300 rpm and a ventilation ratio of 1:0.2. After 12 hours of fermentation, 1.8 L of the seed liquid of *Bacillus* sp. OMK-69 obtained in step (2) was inoculated into the fermentation culture medium, the stirring rotation speed was adjusted to 400 rpm, the ventilation ratio was adjusted to 1:0.4, continually culturing for 10 hours; then the amount of 7 g/L of eugenol, functioning as a substrate, was added, an extra 7 g/L of eugenol was supplemented 4 hours after adding the substrate, 7 g/L of eugenol substrate was supplemented in the following fermentation process every 4 hours in the same way, in total 6 times, so the cumulative amount of eugenol added was 42 g/L (504 g in total), a final vanillin fermentation unit was 35 g/L, and the mass conversion rate of eugenol was 83.3%. The result is shown in FIG. 7.

Compositions of the fermentation culture medium are shown in Table 5:

TABLE 5

| NAME | Concentration(g/L) |
|---|---|
| glucose | 30 |
| yeast powder | 20 |
| peptone | 15 |
| magnesium sulfate | 0.3 |
| potassium dihydrogen phosphate | 1.0 |
| sodium chloride | 0.8 |
| ammonium sulfate | 1.0 |
| pH | nature |

The aforementioned embodiments are merely some embodiments of the present disclosure, and the scope of the disclosure is not limited thereto. Thus, it is intended that the present disclosure cover any modifications and variations of the presently presented embodiments provided they are made without departing from the appended claims and the specification of the present disclosure.

What is claimed is:

1. A method for preparing vanillin by fermentation with eugenol as a substrate, comprising:
preparing vanillin by a mixed fermentation of *Penicillium simplicissimum* OMK-68 and *Bacillus* sp. OMK-69 using eugenol as a substrate, wherein:
the *Penicillium simplicissimum* OMK-68 was deposited at the China Center for Type Culture Collection (CCTCC) with the deposit number of CCTCC NO: M 2019827, and
the *Bacillus* sp. OMK-69 was deposited at the China Center for Type Culture Collection (CCTCC) with the deposit number of CCTCC NO: M 2019826.

2. The method according to claim 1, comprising:
(1) culturing the *Penicillium simplicissimum* OMK-68 and the *Bacillus* sp. OMK-69 on sterile yeast extract peptone dextrose (YPD) plates, and then activating by a first seed culture medium and a second seed culture medium respectively to obtain *Penicillium simplicissimum* OMK-68 seed liquid and *Bacillus* sp. OMK-69 seed liquid;
(2) inoculating the *Penicillium simplicissimum* OMK-68 seed liquid into a sterile fermentation culture medium, and fermenting to obtain a first material in a fermenter for 10-13 hours;
(3) inoculating the *Bacillus* sp. OMK-69 seed liquid into the first material obtained in step (2), and continually fermenting to obtain a second material in the fermenter for 9-11 hours;
(4) adding eugenol, functioning as a first addition, into the second material obtained in step (3), then adding the same amount of eugenol as the first addition every 3-5 hours for 5-7 times in total to obtain a third material, and a cumulative amount of eugenol is 39-45 g/L; and
(5) purifying the third material obtained in step (4) to obtain the vanillin.

3. The method according to claim 2, wherein:
a composition of the first seed culture medium comprises: 28-32 g/L malt extract, 13-16 g/L yeast powder, 8-12 g/L peptone, 1.1-1.3 g/L potassium dihydrogen phosphate, 0.7-0.9 g/L sodium chloride, and
a solvent is water.

4. The method according to claim 2, wherein:
a composition of the second seed culture medium comprises: 18-22 g/L glucose, 9-11 g/L yeast powder, 8-12 g/L peptone, 0.7-0.9 g/L dipotassium hydrogen phosphate, 0.7-0.9 g/L sodium chloride, and
a solvent is water.

5. The method according to claim 2, wherein:
a composition of the sterile fermentation culture medium comprises 28-32 g/L glucose, 18-21 g/L yeast powder, 14-16 g/L peptone, 0.25-0.32 g/L magnesium sulfate, 0.9-1.1 g/L potassium dihydrogen phosphate, 0.7-0.9 g/L sodium chloride, 0.9-1.1 g/L ammonium sulfate, and
a solvent is water.

6. *Penicillium simplicissimum* OMK-68 deposited at the China Center for Type Culture Collection, with the deposit number of CCTCC NO: M 2019827.

7. A method comprising:
fermenting the *Penicillium simplicissimum* OMK-68 according to claim 6 in a preparation of coniferyl alcohol using eugenol as a substrate.

8. *Bacillus* sp. OMK-69 deposited at the China Center for Type Culture Collection, with the deposit number of CCTCC NO: M 2019826.

9. A method comprising:
fermenting the *Bacillus* sp. OMK-69 according to claim 8 in a preparation of vanillin using coniferyl alcohol as a substrate.

10. The method according to claim 3, wherein:
a composition of the sterile fermentation culture medium comprises 28-32 g/L glucose, 18-21 g/L yeast powder, 14-16 g/L peptone, 0.25-0.32 g/L magnesium sulfate, 0.9-1.1 g/L potassium dihydrogen phosphate, 0.7-0.9 g/L sodium chloride, 0.9-1.1 g/L ammonium sulfate, and
a solvent is water.

11. The method according to claim 4, wherein:
a composition of the sterile fermentation culture medium comprises 28-32 g/L glucose, 18-21 g/L yeast powder, 14-16 g/L peptone, 0.25-0.32 g/L magnesium sulfate, 0.9-1.1 g/L potassium dihydrogen phosphate, 0.7-0.9 g/L sodium chloride, 0.9-1.1 g/L ammonium sulfate, and
a solvent is water.

* * * * *